(12) United States Patent
Mattke et al.

(10) Patent No.: US 9,006,481 B2
(45) Date of Patent: Apr. 14, 2015

(54) PROCESS AND APPARATUS FOR PREPARING ISOCYANATES

(75) Inventors: Torsten Mattke, Freinsheim (DE); Carsten Knoesche, Niederkirchen (DE); Bernd Rumpf, Hockenheim (DE); Eckhard Stroefer, Mannheim (DE)

(73) Assignee: BASF SE, Ludwigshafen (DE)

( * ) Notice: Subject to any disclaimer, the term of this patent is extended or adjusted under 35 U.S.C. 154(b) by 715 days.

(21) Appl. No.: 13/256,541

(22) PCT Filed: Mar. 18, 2010

(86) PCT No.: PCT/EP2010/053527
§ 371 (c)(1),
(2), (4) Date: Sep. 14, 2011

(87) PCT Pub. No.: WO2010/106131
PCT Pub. Date: Sep. 23, 2010

(65) Prior Publication Data
US 2012/0004446 A1  Jan. 5, 2012

(30) Foreign Application Priority Data
Mar. 20, 2009 (EP) .................... 09155751

(51) Int. Cl.
C07C 263/00 (2006.01)
C07B 43/10 (2006.01)
C07C 263/10 (2006.01)
F28D 7/00 (2006.01)
F28D 13/00 (2006.01)

(52) U.S. Cl.
CPC ........ C07B 43/10 (2013.01); B01J 2219/00873 (2013.01); C07C 263/10 (2013.01); F28D 7/00 (2013.01); F28D 13/00 (2013.01)

(58) Field of Classification Search
None
See application file for complete search history.

(56) References Cited

U.S. PATENT DOCUMENTS 4,847,408 A    7/1989  Frosch et al.
6,838,578 B2 * 1/2005  Leimkuhler et al. .......... 560/330
6,974,880 B2 * 12/2005 Biskup et al. ................. 560/347
7,019,164 B2 * 3/2006  Friedrich et al. .............. 560/347
8,097,751 B2 * 1/2012  Koch et al. .................... 560/347
8,692,016 B2 * 4/2014  Sanders et al. ................ 560/347
2003/0013909 A1 1/2003 Leimkuhler et al.
2003/0114705 A1 6/2003 Friedrich et al.
2004/0167354 A1 8/2004 Biskup et al.
2006/0025556 A1 2/2006 Koch et al.
2007/0043233 A1 2/2007 Sanders et al.
2009/0149672 A1 6/2009 Pohl et al.

FOREIGN PATENT DOCUMENTS

| EP | 1 275 639 | 1/2003 |
| EP | 1 319 655 | 6/2003 |
| EP | 1 555 258 | 7/2005 |
| EP | 1 616 857 | 1/2006 |
| EP | 1 754 698 | 2/2007 |
| EP | 1 449 826 | 12/2008 |
| EP | 2 062 876 | 5/2009 |
| JP | 63-280050 A | 11/1988 |
| WO | 2010 052230 | 5/2010 |
| WO | 2010 100221 | 9/2010 |

OTHER PUBLICATIONS

U.S. Appl. No. 13/266,049, filed Oct. 24, 2011, Stroefer, et al.
U.S. Appl. No. 13/163,928, filed Jun. 20, 2011, Rosendahl, et al.
International Search Report Issued Nov. 2, 2010 in PCT/EP10/053527 filed Mar. 18, 2010.
U.S. Appl. No. 13/380,357, filed Dec. 22, 2011, Schelling, et al.
U.S. Appl. No. 13/383,549, filed Jan. 11, 2012, Schelling, et al.
U.S. Appl. No. 13/383,433, filed Jan. 11, 2012, Schelling, et al.

* cited by examiner

*Primary Examiner* — Sudhakar Katakam
(74) *Attorney, Agent, or Firm* — Oblon, McClelland, Maier & Neustadt, L.L.P.

(57) ABSTRACT

The invention relates to a process for preparing isocyanates by reacting the corresponding amines with phosgene in the gas phase, optionally in the presence of an inert medium, in which phosgene and amine are first evaporated and then superheated further to reaction temperature, and the superheated phosgene and amine are mixed and fed to a reactor in which the phosgene and the amine are converted to the isocyanate, wherein the residence time of the phosgene at temperatures greater than 300° C. is not more than 5 s, and/or the temperature of heat transfer surfaces in contact with phosgene is not more than 20 K above the phosgene temperature to be established. The invention further relates to an apparatus for preparing isocyanates by reacting the corresponding amines with phosgene in the gas phase.

10 Claims, No Drawings

PROCESS AND APPARATUS FOR PREPARING ISOCYANATES

CROSS REFERENCE TO RELATED APPLICATIONS

This application is the National Stage of PCT/EP10/053,527, filed Mar. 18, 2010, the disclosure of which is incorporated herein by reference in its entirety. This application claims priority to European Application No. 09155751.2, filed Mar. 20, 2009, the disclosure of which is incorporated herein by reference in its entirety.

The invention relates to a process for preparing isocyanates by reacting the corresponding amines with phosgene in the gas phase, optionally in the presence of an inert medium, in which phosgene and amine are first evaporated and then superheated further to reaction temperature, and the superheated phosgene and amine are mixed and fed to a reactor in which the phosgene and the amine are converted to the isocyanate. The invention further relates to an apparatus for preparing isocyanates by reacting the corresponding amines with phosgene in the gas phase, optionally in the presence of an inert medium, comprising a reactor into which an apparatus for mixing amine and phosgene opens, and apparatus for evaporation and for superheating of phosgene and amine.

Isocyanates can in principle be prepared by phosgenating the corresponding amines by a liquid phase phosgenation or a gas phase phosgenation. In gas phase phosgenation, a higher selectivity, a lower holdup of toxic phosgene and a reduced amount of energy are required.

In gas phase phosgenation, an amine-containing reactant stream and a phosgene-containing reactant stream are mixed, each in the gaseous state. The amine and the phosgene react with release of hydrogen chloride (HCl) to give the corresponding isocyanates. The amine-containing reactant stream is generally present in the liquid phase and has to be evaporated and if appropriate superheated before being mixed with the phosgene-containing stream.

Corresponding processes for preparing isocyanates in the gas phase are described, for example, in EP-A 1 319 655 or EP-A 1 555 258.

The evaporation and superheating of amine and phosgene to reaction temperature can be effected either by total evaporation of the particular reactant stream required or else by partial evaporation of a liquid stream with recycling of the remaining condensed fraction to the evaporator inlet.

Especially in the case of superheating of the phosgene, there may, however, according to the corresponding chemical equilibrium, be redissociation of the carbamoyl chloride to chlorine and carbon monoxide. For example, according to Atkinson et al., J. Chem. Soc. Trans. 117, Vol. II, 1920, page 1410, about 0.2% of the phosgene is present in dissociated form at 210° C. and standard pressure. At 355° C., however, already about 10% is present in dissociated form. However, the chlorine present in the phosgene stream has the disadvantage that the isocyanate is chlorinated in the reactor at a reaction temperature in the range from 360 to 450° C. This leads, however, to quality problems. For example, in the preparation of hexamethylene diisocyanate, chlorinated components are held responsible for color problems in the product.

It is therefore an object of the present invention to provide a process for preparing isocyanates by reacting the corresponding amines with phosgene, in which redissociation of the carbamoyl chloride to chlorine and carbon monoxide is reduced or even prevented.

The object is achieved by a process for preparing isocyanates by reacting the corresponding amines with phosgene in the gas phase, optionally in the presence of an inert medium, in which phosgene and amine are first evaporated and then superheated further to reaction temperature, and the superheated phosgene and amine are mixed and fed to a reactor in which the phosgene and the amine are converted to the isocyanate. The process has at least one of the following features:

(a) the residence time of the phosgene at temperatures greater than 300° C. is not more than 5 s,
(b) the temperature of heat transfer surfaces in contact with phosgene is not more than 20 K above the phosgene temperature to be established.

The residence time of the phosgene in plant parts with high temperature, i.e. a temperature of more than 300° C., of less than 5 s, preferably less than 2.5 s, has the advantage that, owing to the low thermal stress realized as a result, the dissociation of the phosgene to chlorine and carbon monoxide can be reduced.

A residence time of the phosgene of less than 5 s, preferably of less than 2.5 s, at temperatures of more than 300° C. is achieved, for example, by comparatively rapid superheating of the phosgene. Comparatively rapid superheating is achieved, for example, when the evaporation and superheating of the phosgene is performed in a common heat exchanger with a ratio of evaporator surface area to volume of more than 750 1/m. The ratio of evaporator surface area to volume of more than 750 1/m achieves rapid heat transfer and hence rapid heating of the phosgene. This likewise allows the residence time to be reduced and the dissociation of phosgene to carbon monoxide and chlorine to be reduced, in order thus to minimize the chlorine content in the reactant stream.

Since the dissociation of the phosgene to chlorine and carbon monoxide increases with rising temperature, it is additionally preferred to superheat the phosgene to a temperature of less than 500° C., preferably less than 450° C. and especially less than 400° C. This measure likewise allows the dissociation of the phosgene to chlorine and carbon monoxide to be reduced.

The temperature needed for the reaction of phosgene and amine to give the isocyanate is generally in the range from 250 to 550° C., especially in the range from 300 to 500° C. The pressure at which the reaction is performed is preferably in the range between 0.3 and 3 bar absolute, more preferably in the range from 0.8 to 3.0 bar absolute.

The heating to the required reaction temperature preferably precedes the mixing of phosgene and amine, since, for avoidance of reaction by-products, a short residence time of the reaction mixture at reaction temperature is desirable in order to prevent decomposition or further reaction of the isocyanate.

The heating of the phosgene and of the amine before they are mixed can be effected, for example, by electrical heating or direct or indirect heating by combustion of a fuel, or else by heat exchange with a heating medium. When the heating is effected by combusting a fuel, typically fuel gases, for example natural gas, are used. Suitable examples for heating with a heating medium include heat carrier oils or else steam. In the case of use of steam, multistage heating is typically effected, for which steam with different pressures and different temperatures can be used. However, the phosgene and the amine are then typically superheated with a heat carrier oil or, for example, by electrical heating or direct or indirect heating by combusting a fuel. When steam is used to evaporate the phosgene and heat the amine, the vapor pressure of the steam is, for example, in the range from 40 to 100 bar. This gives rise to a temperature of the steam in the range from 250 to 311° C., unless superheated steam is used.

In the course of evaporation and superheating of the phosgene and of the amine, hotspots should be avoided. Particular preference is therefore given to evaporating and superheating by using a heating medium.

The reactor which is used for phosgenation of the amine to prepare isocyanates is known to those skilled in the art. In general, the reactors used are tubular reactors. In the reactor, the amine is reacted with the phosgene to give the corresponding isocyanate and hydrogen chloride. Typically, the phosgene is added in excess, such that the reaction gas which forms in the reactor, as well as the isocyanate formed and the hydrogen chloride, also comprises phosgene.

Amines which can be used to prepare isocyanates are monoamines, diamines, triamines or higher-functionality amines. Preference is given to using monoamines or diamines. According to the amine used, the corresponding monoisocyanates, diisocyanates, triisocyanates or higher-functionality isocyanates are formed. Preference is given to preparing monoisocyanates or diisocyanates by the process according to the invention.

Diamines and diisocyanates may be aliphatic, cycloaliphatic or aromatic.

Cycloaliphatic isocyanates are those which comprise at least one cycloaliphatic ring system.

Aliphatic isocyanates are those which have exclusively isocyanate groups which are bonded to straight or branched chains.

Aromatic isocyanates are those which have at least one isocyanate group bonded to at least one aromatic ring system.

The term "(cyclo)aliphatic isocyanates" is used hereinafter for cycloaliphatic and/or aliphatic isocyanates.

Examples of aromatic monoisocyanates and diisocyanates are preferably those having from 6 to 20 carbon atoms, for example phenyl isocyanate, monomeric methylene 2,4'- and/or 4,4'-di(phenyl isocyanate) (MDI), tolylene 2,4- and/or 2,6-diisocyanate (TDI) and naphthyl 1,5- or 1,8-diisocyanate (NDI).

Examples of (cyclo)aliphatic diisocyanates are aliphatic diisocyanates such as tetramethylene 1,4-diisocyanate, hexamethylene 1,6-diisocyanate (1,6-diisocyanatohexane), octamethylene 1,8-diisocyanate, decamethylene 1,10-diisocyanate, dodecamethylene 1,12-diisocyanate, tetradecamethylene 1,14-diisocyanate, 1,5-diisocyanatopentane, neopentane diisocyanate, derivatives of lysine diisocyanate, tetramethylxylylene diisocyanate (TMXDI), trimethylhexane diisocyanate or tetramethylhexane diisocyanate, and also 3(or 4),8(or 9)-bis(isocyanatomethyl)tricyclo[5.2.1.0$^{2,6}$]decane isomer mixtures, and also cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane, 2,4- or 2,6-diisocyanato-1-methylcyclohexane.

Preferred (cyclo)aliphatic diisocyanates are 1,6-diisocyanatohexane, 1-isocyanato-3,3,5-trimethyl-5-(isocyanatomethyl)cyclohexane and 4,4'-di(isocyanatocyclohexyl)methane. Particular preference is given to 1,6-diisocyanatohexane, 1-isocyanato-3,3,5-trimethyl-5-(isocyanatomethyl)cyclohexane, 1,5-diisocyanatopentane and 4,4'-di(isocyanatocyclohexyl)methane.

Examples of aromatic diisocyanates are tolylene 2,4-, 2,6-diisocyanate, methylenediphenyl isocyanate or isomer mixtures thereof.

Amines which are used in the process according to the invention for the reaction to give the corresponding isocyanates are those for which the amine, the corresponding intermediates and the corresponding isocyanates are present in gaseous form under the selected reaction conditions. Preference is given to amines which, during the reaction, decompose under the reaction conditions to an extent of at most 2 mol %, more preferably to an extent of at most 1 mol % and most preferably to an extent of at most 0.5 mol %. Particularly suitable here are amines, especially diamines, based on aliphatic or cycloaliphatic hydrocarbons having from 2 to 18 carbon atoms. Examples thereof are 1,6-diaminohexane, 1,5-diaminopentane, 1,3-bis(aminomethyl)-cyclohexane, 1-amino-3,3,5-trimethyl-5-aminomethylcyclohexane (IPDA) and 4,4-diaminodicyclohexylmethane. Preference is given to using 1,6-diaminohexane (HDA) and 1,5-diaminopentane.

It is likewise possible to use aromatic amines for the process according to the invention, which can be converted to the gas phase without significant decomposition. Examples of preferred aromatic amines are tolylenediamine (TDA), as the 2,4- or 2,6-isomer or as a mixture thereof, for example as an 80:20 to 65:35 (mol/mol) mixture, diaminobenzene, 2,6-xylidine, naphthyldiamine (NDA) and 2,4'- or 4,4'-methylene (diphenyldiamine) (MDA) or isomer mixtures thereof. Among these, preference is given to the diamines, particular preference to 2,4- and/or 2,6-TDA or 2,4'- and/or 4,4'-MDA.

To prepare monoisocyanates, it is likewise possible to use aliphatic, cycloaliphatic or aromatic amines, typically monoamines. A preferred aromatic monoamine is especially aniline.

In the gas phase phosgenation, the aim is that the compounds which occur in the course of the reaction, i.e. reactants (amine and phosgene), intermediates (especially the mono- and dicarbamoyl chlorides which form as intermediates), end products (isocyanate), and any inert compounds metered in, remain in the gas phase under the reaction conditions. Should these or other components be deposited out of the gas phase, for example on the reactor wall or other apparatus components, these depositions can undesirably alter the heat transfer or the flow of the components in question. This is especially true of the occurrence of amine hydrochlorides, which form from free amino groups and hydrogen chloride, since the resulting amine hydrochlorides precipitate out readily and are reevaporable only with difficulty.

In addition to the use of a tubular reactor, it is also possible to use essentially cuboidal reaction chambers, for example plate reactors. Any other cross section of the reactor is also possible.

In order to prevent the formation of by-products, it is preferred to supply phosgene in excess. In order to supply only the proportion of amines needed for the reaction, it is possible to mix the amine with an inert gas. Through the proportion of inert gas in the amine, it is possible to adjust the amount of the amine supplied for a given geometry of the feed orifices for the amine and the phosgene. Inert media which can be added are those which are present in gaseous form in the reaction chamber and do not react with the compounds which occur in the course of the reaction. The inert media used may, for example, be nitrogen, noble gases such as helium or argon, aromatics such as chlorobenzene, o-dichlorobenzene, trichlorobenzene, toluene, xylene, chloronaphthalene, decahydronaphthalene, carbon dioxide or carbon monoxide. Preference is given, however, to using nitrogen and/or chlorobenzene as the inert medium.

Alternatively, it is, however, also possible, for example in order to avoid too great an excess of phosgene, to add the inert medium to the phosgene.

In general, the inert medium is added in an amount such that the ratio of the gas volumes of inert medium to amine or to phosgene is less than 0.0001 to 30, preferably less than 0.01 to 15 and more preferably less than 0.1 to 5.

In order to reduce or to prevent the formation of undesired by-products and also to suppress decomposition of the isocyanate formed, the reaction gas is cooled in a quench immediately after the reaction. To this end, a preferably liquid quench medium is added. As a result of heating or evaporation of the quench medium, it absorbs heat and leads to rapid cooling of the reaction gas.

Phosgene and amine are mixed, for example, in a mixing nozzle with which amine and phosgene are supplied to the reactor. Alternatively, it is also possible to supply amine and phosgene via suitable nozzles to a mixing chamber in which they are mixed and then flow further into the reactor. Preference is given, however, to the use of a mixing nozzle.

In order to achieve the desired short residence time of the phosgene at high temperatures, i.e. at temperatures of more than 300° C., of less than 5 seconds, it is possible to use various heat exchanger types, for example micro or milli heat exchangers, tube bundle heat exchangers, fluidized bed heat exchangers, microwave superheaters or heat radiators. Especially preferred are heat exchangers with a volume-specific evaporator surface area of more than 750 1/m, since the residence time of the phosgene at high temperatures can be kept low in such heat exchangers. In addition, the temperature difference between exchanger surface and the phosgene stream can be minimized. It is particularly advantageous to use micro heat exchangers, since phosgene forms barely any deposits which can lead to blockages of the micro heat exchanger.

For evaporation and superheating of the phosgene, preference is given, however, to using at least one tube bundle heat exchanger. The tube bundle heat exchanger may or may not be equipped with turbulence-generating internals or attachments. When the phosgene is conducted into the tubes of the tube bundle heat exchanger, suitable internals are, for example, twisted lengths, increased wall roughness, hiTRAN elements, mesh networks, twisted tapes or other turbulence generators known to those skilled in the art. If the phosgene is to flow around the tubes, it is possible to use, for example, fins or ribs. The use of turbulence-generating internals reduces the necessary wall superheating and the required residence time to superheat the phosgene. In this way, the thermal stress on the phosgene stream falls.

In one embodiment, a heating register with transverse flow is used to superheat the phosgene. The tubes of the heating register with transverse flow may be configured with or without ribbing. It is also conceivable to perform the superheating in a plurality of heating registers in stages. For flow homogenization, packings can be installed between the individual heating registers.

Likewise suitable for evaporation and superheating of the phosgene are helical tubes. The secondary flows generated in helical tubes bring about a high heat transfer coefficient and hence low wall temperatures and short residence times. It is also possible to use additional internals in a helical tube for improvement of the heat transfer, for example turbulence generators.

In addition to tube bundle heat exchangers, it is also possible to use plate heat exchangers. In this case, especially thermoplate heat exchangers are used. In the case of use of thermoplate heat exchangers too, the heat transfer can be intensified and hence the wall temperatures and the residence times can be reduced by using internals.

Further suitable heat exchangers are, for example, fluidized bed heat exchangers, microwave superheaters and heat radiators. These designs too each allow low wall superheating and short residence times of the phosgene, and thus enable reduction of the dissociation of the phosgene to chlorine and carbon monoxide.

An apparatus suitable for preparing isocyanates by reacting the corresponding amines with phosgene in the gas phase, optionally in the presence of an inert medium, comprises a reactor, an apparatus for mixing amine and phosgene which opens into the reactor, and apparatus for evaporation and for superheating of phosgene and amine. The apparatus for evaporation and/or superheating of the phosgene is a heat exchanger with a ratio of evaporator surface area to volume of more than 750 1/m.

As already described above, a heat exchanger with a ratio of evaporator surface area to volume of more than 750 1/m can achieve a residence time of the phosgene of less than 5 seconds at temperatures of more than 300° C. This allows reduction of the dissociation of the phosgene to carbon monoxide and chlorine, and improvement in the product quality of the isocyanate to be prepared, since the formation of by-products is reduced by reaction with chlorine.

Suitable heat exchangers which have a ratio of evaporator surface area to volume of more than 750 1/m are, for example, milli or micro heat transfers.

For evaporation and/or superheating of the phosgene, preference is given, however, to using a tube bundle heat exchanger which has a ratio of evaporator surface area to volume of more than 750 1/m. The appropriate ratio can be achieved, for example, in the case of flow of the phosgene to be heated through the tubes of the tube bundle heat exchanger, through the tube diameter and any internals in the tubes. To improve the heat transfer, it is preferred, as already described above, when turbulence generators are arranged in the tubes.

In order to reduce the residence time of the phosgene at high temperatures, it is preferred when the evaporation and superheating of the phosgene are performed in the same heat exchanger. This allows pipelines between individual evaporators to be dispensed with and the distances to be shortened. This simultaneously leads to a reduction in the residence time. For gentle evaporation and superheating of the phosgene, it is preferred when the heat exchanger has a plurality of heating registers in which the phosgene is evaporated and superheated stepwise. The heating registers can be operated with different heating media. For example, for evaporation of the phosgene, it is possible to use a heating register through which steam with a pressure of approx. 4 bar flows as the heating medium. This may be followed downstream by a further heating register through which, for example, steam with a pressure in the range from 16 to 40 bar flows. The steam with a pressure in the range from 16 to 40 bar typically has a higher temperature than the steam of 4 bar, such that this achieves further heating. This may be followed downstream by a further heating register through which, for example, a heat carrier oil flows. The use of heat carrier oils typically allows higher temperatures than the use of steam. It is also possible to use, for example, an ionic liquid or a salt melt as the heating medium. An advantage of the use of a heating medium is especially that hotspots and hence local overheating, which can lead to rapid dissociation of the phosgene to chlorine and carbon monoxide, are avoided.

A further reduction in the residence time is also achieved when the apparatus for mixing phosgene and amine follows directly downstream of the apparatus for superheating the phosgene. In this way, it is likewise possible to dispense with flow pipelines and hence to reduce the flow time and the residence time of the phosgene at reaction temperature.

The invention claimed is:

1. A process for preparing isocyanates, comprising:
evaporating phosgene and an amine; then
superheating the evaporated phosgene and the evaporated amine to a reaction temperature;
mixing the superheated phosgene and the superheated amine and then feeding the resulting superheated mixture to a reactor; and
reacting the phosgene and the amine in the gas phase, optionally in the presence of an inert medium, to obtain an isocyanate,
wherein (a) a residence time of the phosgene at temperatures greater than 300° C. is not more than 5 s, (b) a temperature of heat transfer surfaces in contact with the phosgene is not more than 20 K above the phosgene temperature to be established, or a combination thereof.

2. The process of claim 1, wherein the phosgene is evaporated and/or superheated in a micro or milli heat exchanger, a tube bundle heat exchanger, a fluidized bed heat exchanger, a microwave superheater or a heat radiator.

3. The process of claim 1, wherein the evaporation, the superheating, or both, of the phosgene are performed in the same apparatus.

4. The process of claim 1, wherein the evaporation and the superheating of the phosgene occur in a plurality of stages.

5. The process of claim 1, wherein the phosgene is added to the reactor in excess.

6. The process of claim 1, wherein the amine added to the reactor is further mixed with an inert gas.

7. The process of claim 2, wherein the evaporation, the superheating, or both, of the phosgene are performed in the same apparatus.

8. The process of claim 2, wherein the evaporation and the superheating of the phosgene occur in a plurality of stages.

9. The process of claim 2, wherein the phosgene is added to the reactor in excess.

10. The process of claim 2, wherein the amine added to the reactor is further mixed with an inert gas.

* * * * *